(12) United States Patent
Asfora et al.

(10) Patent No.: US 10,631,905 B2
(45) Date of Patent: Apr. 28, 2020

(54) BONE CAGE WITH HELICALLY ARRANGED FENESTRATIONS

(71) Applicant: SICAGE LLC, Sioux Falls, SD (US)

(72) Inventors: Wilson Theophilo Asfora, Sioux Falls, SD (US); Daniel S. Savage, Brecksville, OH (US)

(73) Assignee: SICAGE LLC, Sioux Falls, SD (US)

( * ) Notice: Subject to any disclaimer, the term of this patent is extended or adjusted under 35 U.S.C. 154(b) by 228 days.

(21) Appl. No.: 15/798,984

(22) Filed: Oct. 31, 2017

(65) Prior Publication Data
US 2019/0125408 A1    May 2, 2019

(51) Int. Cl.
*A61B 17/86*    (2006.01)

(52) U.S. Cl.
CPC ........ *A61B 17/8625* (2013.01); *A61B 17/864* (2013.01); *A61B 17/863* (2013.01); *A61B 17/8635* (2013.01)

(58) Field of Classification Search
CPC ... A61B 17/86; A61B 17/8605; A61B 17/861; A61B 17/8625; A61B 17/863; A61B 17/8635; A61B 17/864
USPC .............................. 606/604, 311, 312, 323
See application file for complete search history.

(56) References Cited

U.S. PATENT DOCUMENTS

| | | | |
|---|---|---|---|
| 1,563,574 A | 12/1925 | Jensen | |
| 2,243,718 A | 5/1941 | Moreira | |
| 2,943,624 A | 7/1960 | Alquist | |
| 3,844,318 A | 10/1974 | Raia et al. | |
| 4,563,178 A | 1/1986 | Santeramo | |
| 5,061,181 A | 10/1991 | Niznick | |
| 5,334,205 A | 8/1994 | Cain | |
| 5,676,545 A | 10/1997 | Jones | |
| 5,725,581 A * | 3/1998 | Brånemark | A61F 2/30721 606/304 |
| 5,735,898 A | 4/1998 | Branemark | |
| 5,743,916 A | 4/1998 | Greenberg et al. | |
| D411,009 S | 6/1999 | Asfora | |
| 6,030,162 A | 2/2000 | Huebner | |
| 6,135,772 A | 10/2000 | Jones | |
| 6,149,686 A | 11/2000 | Kuslich et al. | |
| 6,287,343 B1 | 9/2001 | Kuslich et al. | |
| 6,391,058 B1 | 5/2002 | Kuslich et al. | |
| 6,517,542 B1 | 2/2003 | Papay et al. | |

(Continued)

FOREIGN PATENT DOCUMENTS

| | | |
|---|---|---|
| WO | 2014/026134 A2 | 2/2014 |
| WO | 2014149746 A1 | 9/2014 |

OTHER PUBLICATIONS

International Application PCT/US2018/058543, filed Oct. 31, 2018 Search Report and Written Opinion, dated May 21, 2019.

*Primary Examiner* — Eric S Gibson
(74) *Attorney, Agent, or Firm* — Fox Rothschild LLP

(57) ABSTRACT

Disclosed herein is a bone cage that includes a shaft extending from a head to a tapered tip and including threads disposed on an external surface of the shaft. The cage also includes a plurality of fenestrations defining a row disposed in at least a first helix along at least a portion of the shaft, each of the plurality of fenestrations extend directly through a natural portion of the thread. The cage also includes a cannula positioned within the shaft and extending from an opening in the head to another opening in the tip. Each of the fenestrations are defined by a wall that extends from the exterior of the shaft to the cannula.

34 Claims, 11 Drawing Sheets

(56) References Cited

U.S. PATENT DOCUMENTS

| | | |
|---|---|---|
| 6,554,830 B1 | 4/2003 | Chappius |
| 6,565,572 B2 | 5/2003 | Chappius |
| 6,604,945 B1 | 8/2003 | Jones |
| 6,755,835 B2 | 6/2004 | Schultheiss et al. |
| 7,354,442 B2 | 4/2008 | Sasso et al. |
| D578,218 S | 10/2008 | Purga |
| D588,699 S | 3/2009 | Aldecoa |
| 7,527,611 B2 | 5/2009 | Sweeney |
| 7,575,572 B2 | 8/2009 | Sweeney |
| D601,703 S | 10/2009 | Kahdemann |
| 7,608,062 B2 | 10/2009 | Sweeney |
| D603,513 S | 11/2009 | Emanuelli |
| D604,851 S | 11/2009 | Ishikawa |
| D605,291 S | 12/2009 | Ishikawa |
| 7,717,947 B1 | 5/2010 | Wilberg et al. |
| D620,117 S | 7/2010 | Dawson |
| 8,062,270 B2 | 11/2011 | Sweeney et al. |
| D659,247 S | 5/2012 | Lussi |
| D667,548 S | 9/2012 | Brannon |
| D668,764 S | 10/2012 | Lussi |
| 8,303,602 B2 | 11/2012 | Biedermann et al. |
| 8,382,808 B2 | 2/2013 | Wilberg et al. |
| 8,574,273 B2 * | 11/2013 | Russell .............. A61B 17/0401 606/304 |
| 8,764,797 B2 | 7/2014 | Dreyfuss et al. |
| 8,808,337 B2 | 8/2014 | Sweeney et al. |
| 8,870,836 B2 | 10/2014 | Sweeney |
| 8,945,193 B2 * | 2/2015 | Kirschman ........ A61B 17/7064 606/304 |
| 8,956,369 B2 | 2/2015 | Millett et al. |
| 8,992,587 B2 * | 3/2015 | Kirschman ........ A61B 17/7064 606/305 |
| 9,055,986 B1 * | 6/2015 | Whipple .............. A61B 17/863 |
| 9,131,970 B2 | 9/2015 | Kang |
| 9,173,692 B1 | 11/2015 | Kaloostian |
| 9,198,702 B2 | 12/2015 | Biederman et al. |
| D748,263 S | 1/2016 | Ishiwata |
| 9,265,540 B2 * | 2/2016 | Kirschman ........ A61B 17/7064 |
| 9,271,742 B2 | 3/2016 | Asfora |
| 9,271,743 B2 | 3/2016 | Asfora |
| 9,295,488 B2 | 3/2016 | Asfora |
| 9,326,779 B2 | 5/2016 | Dorawa et al. |
| 9,326,801 B2 | 5/2016 | Poulos |
| 9,333,018 B2 * | 5/2016 | Russell .............. A61B 17/0401 |
| 9,445,852 B2 | 9/2016 | Sweeney |
| 9,526,548 B2 | 12/2016 | Asfora |
| 9,566,100 B2 | 2/2017 | Asfora |
| 9,616,205 B2 | 4/2017 | Nebosky et al. |
| 9,642,656 B2 | 5/2017 | Kotuljac et al. |
| 10,179,014 B1 * | 1/2019 | Menmuir ........... A61B 17/8605 |
| 2001/0004694 A1 * | 6/2001 | Carchidi ............ A61B 17/8615 606/312 |
| 2002/0087161 A1 * | 7/2002 | Randall ................ A61B 17/683 606/916 |
| 2005/0055026 A1 | 3/2005 | Biedermann |
| 2006/0149263 A1 * | 7/2006 | Newcomb .......... A61B 17/8625 606/311 |
| 2006/0247642 A1 * | 11/2006 | Stone ................ A61B 17/0642 623/13.14 |
| 2007/0233123 A1 | 10/2007 | Ahmad et al. |
| 2009/0318981 A1 * | 12/2009 | Kang ................ A61B 17/7098 606/329 |
| 2010/0211118 A1 * | 8/2010 | Christen ............. A61B 17/863 606/312 |
| 2011/0137352 A1 * | 6/2011 | Biedermann ...... A61B 17/8635 606/305 |
| 2011/0137354 A1 * | 6/2011 | Biedermann ........ A61B 17/862 606/312 |
| 2011/0213426 A1 | 9/2011 | Yedlicka et al. |
| 2012/0010659 A1 * | 1/2012 | Angert ............... A61B 17/1757 606/247 |
| 2012/0022603 A1 * | 1/2012 | Kirschman ........ A61B 17/7064 606/305 |
| 2012/0089195 A1 | 4/2012 | Yedlicka et al. |
| 2012/0197311 A1 * | 8/2012 | Kirschman ........ A61B 17/7064 606/304 |
| 2012/0232599 A1 * | 9/2012 | Schoenly ............ A61B 17/863 606/315 |
| 2013/0065698 A1 | 3/2013 | Biedermann et al. |
| 2013/0072986 A1 * | 3/2013 | Robinson ........... A61B 17/8605 606/279 |
| 2013/0237813 A1 * | 9/2013 | Beyar ................ A61B 17/8685 600/424 |
| 2013/0245602 A1 | 9/2013 | Sweeney |
| 2014/0012340 A1 | 1/2014 | Beck et al. |
| 2014/0046381 A1 | 2/2014 | Asfora |
| 2014/0058460 A1 * | 2/2014 | Reed .................. A61B 17/8625 606/312 |
| 2014/0236242 A1 * | 8/2014 | Robinson ........... A61B 17/8605 606/279 |
| 2014/0277188 A1 * | 9/2014 | Poulos ............... A61B 17/1655 606/304 |
| 2015/0230844 A1 | 8/2015 | Ellis |
| 2015/0238203 A1 | 8/2015 | Asfora |
| 2015/0272646 A1 * | 10/2015 | Russell .............. A61B 17/7098 606/304 |
| 2015/0313658 A1 | 11/2015 | Kolb |
| 2015/0320469 A1 | 11/2015 | Biedermann |
| 2016/0000489 A1 | 1/2016 | Kaloostian |
| 2016/0008044 A1 | 1/2016 | Sweeney |
| 2016/0120583 A1 * | 5/2016 | Bales ................. A61B 17/8625 606/304 |
| 2016/0143671 A1 | 5/2016 | Jiminez |
| 2016/0143679 A1 | 5/2016 | Asfora |
| 2016/0143742 A1 | 5/2016 | Asfora |
| 2016/0151100 A1 | 6/2016 | Biedermann et al. |
| 2016/0220291 A1 * | 8/2016 | Russell .............. A61B 17/0401 |
| 2016/0310188 A1 | 10/2016 | Marino et al. |
| 2019/0125408 A1 * | 5/2019 | Asfora ............... A61B 17/8625 |

\* cited by examiner

BONE CAGE WITH HELICALLY ARRANGED FENESTRATIONS

TECHNICAL FIELD

The present invention relates generally to orthopedic surgery. More specifically, techniques associated with a bone cage for joint fusion are described.

BACKGROUND

Stress across joints and in particular the sacroiliac joint generally is a common cause of pain including lower back pain. Various types of sacroiliac joint stress, including sacroiliac joint disruptions (i.e., separations) and degenerative sacroiliitis (i.e., inflammation), can result from lumbar fusion, trauma, postpartum, heavy lifting, arthritis, or unknown causes. Sacroiliac joint fixation or arthrodesis is sometimes recommended for skeletally mature patients with severe, chronic sacroiliac joint pain or acute trauma in the sacroiliac joint.

Conventional solutions for stabilizing joints and relieving pain in joints typically include the insertion of an implant, such as a metal screw, rod or bar, laterally across the joint. Even less invasive procedures have drawbacks. One drawback of conventional solutions for sacroiliac joint fixation is the inability to deliver materials, such as bone regenerative materials, antibiotics, steroids, and other joint treatment materials (i.e., for inflammation or infections), to the bones through implants and an implantation procedures that is minimally invasive. Another drawback of conventional implants for sacroiliac joint fixation is that they do not allow for bone growth into and through the implant for true fusion of the joint. Finally, conventional implantation solutions do not provide methods for delivering such joint stress treatment materials through the implant at a later time (i.e., post-implantation).

SUMMARY

The summary is illustrative only and is not intended to be in any way limiting. In addition to the illustrative aspects, embodiments, and features described above, further aspects, embodiments, and features will become apparent by reference to the drawings and the following detailed description.

In accordance with various embodiments, a bone cage may include a shaft extending from a head to a tapered tip and including threads disposed on an external surface of the shaft. The cage also includes a plurality of fenestrations defining a row disposed in at least a first helix along at least a portion of the shaft, each of the plurality of fenestrations extend directly through a natural portion of the thread. The cage also includes a cannula positioned within the shaft and extending from an opening in the head to another opening in the tip. Each of the fenestrations are defined by a wall that extends from the exterior of the shaft to the cannula.

In accordance with various embodiments, a bone cage may include a shaft extending from a head to a tapered tip and including threads disposed on an external surface of the shaft. The bone cage can also include cannula positioned within the shaft defined by a wall forming the shaft. The cannula extends from an opening in the head to another opening in the tip. The bone cage can also include a plurality of helical rows of fenestrations with each row having three or more fenestrations, wherein each of the fenestrations extends through deferent portions of the threads on the shaft to the cannula and each of the plurality of helical rows extends more longitudinally than circumferentially.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1A:
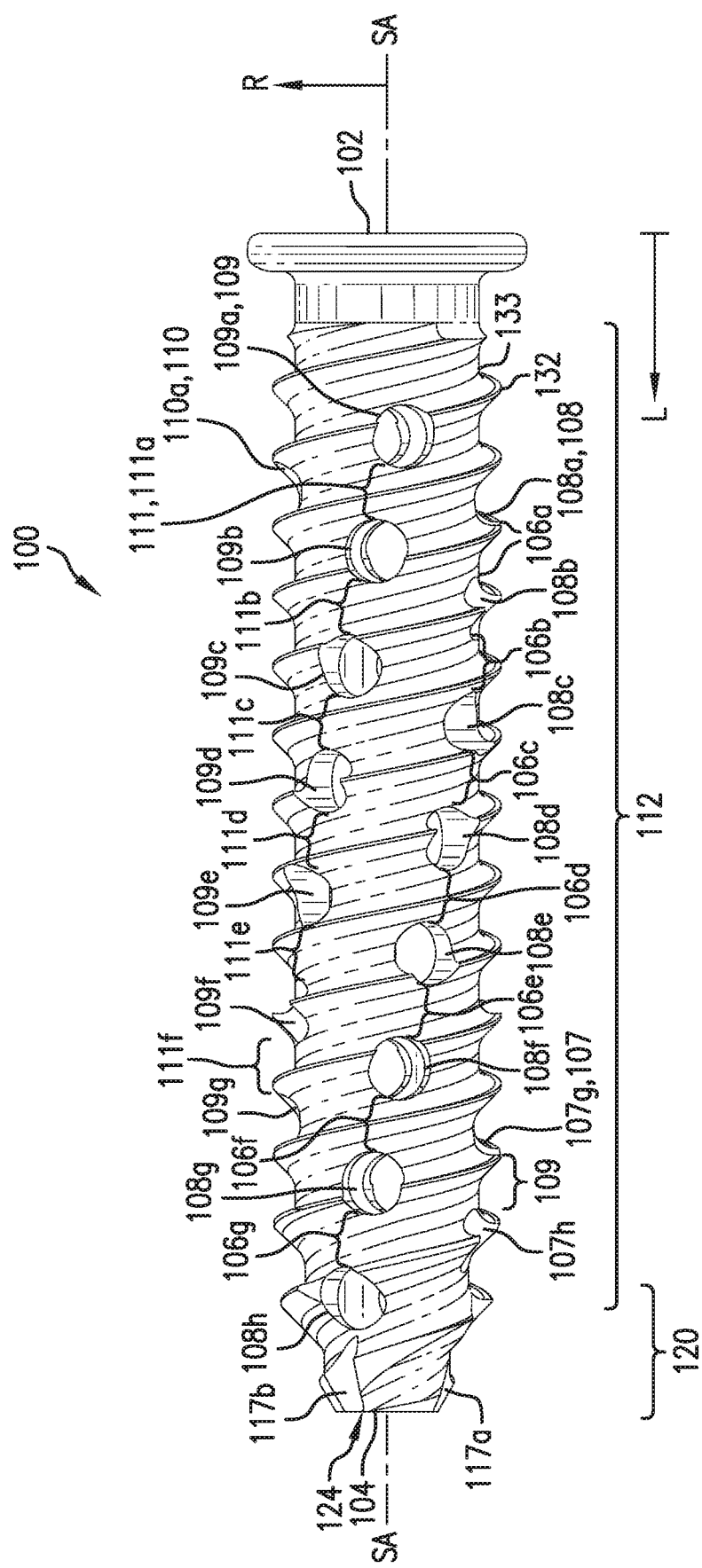
FIG. 1A is a side view of a cage for joint fusion according to one embodiment.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are implicitly contemplated herein.

Techniques for joint fusion are described, including systems, apparatuses and processes for fusing a joint. Systems and apparatuses for fusing a joint include a cage (i.e., a cannulated cage), a tissue protector assembly, a guide pin, a depth gauge, a cannulated drill bit (e.g., an adjustable cannulated drill bit that employs a stop collar), a driver, a parallel spacer instrument, and a plunger distance tool. As used herein, the term "cannulated" refers to having a cannula, or a hollow shaft. In some examples, the cage may be inserted or implanted into tissue (e.g., bone, cartilage, or other tissue in the joint). As used herein, the term "implant" or "implantation" refers to inserting or insertion into a part of a body. For example, a bone cage may be implanted into a joint (e.g., a sacroiliac joint). In some examples, the cage may have a cannula and radial fenestrations in which therapeutic materials may be packed. Such therapeutic materials may include osteogenic compounds (e.g., bone morphogenetic protein, or other osteogenic compounds that may ossify tissue in the joint), osteoconductive materials (e.g., demineralized bone, hydroxyapatite, or other material that promotes bone growth), antibiotics, steroids, contrast materials, or other materials that may beneficial to fusing the joint, treating inflammation or other conditions in the joint, or enabling the visualization of the area within and adjacent to an implanted bone cage. In some examples, the bone cage may be a screw or screw type device having threads. In some examples, the screw may have one or more rows or groups of helical fenestrations along the wall (i.e. the shaft of the cage defining the cannula) of its shaft to allow the material packed inside the cannula of the cage to contact (e.g., touch, seep into, affect, communicate with, or otherwise physically contact) tissue adjacent to, surrounding, or even within, the cage. In some examples, various tools may be used to insert a cage into a location on a joint, and to prepare the location for the insertion procedure. Such tools may include an implantation assembly, which may comprise a tissue protector; a guide pin; a depth gauge; a cannulated drill bit; a driver; a parallel spacer instrument; a packing plunger, which may comprise a packing tube, a plunger and a loading port; a plunger distance tool; and other tools.

In some examples, a guide pin may be inserted first into a joint at a desired location, in a lateral position across the joint. In some examples, a tissue protector assembly may be used, along with the guide pin, to guide the preparation (i.e., drilling) of a pilot hole as well as to guide insertion of a cannulated cage or other implant while forming a barrier between the preparation site and the surrounding tissue. In some examples, a cannulated drill bit may be used with the tissue protector and/or guide pin to drill the pilot hole. In some examples, a driver or screw driver may be used to insert the cage into the pilot hole. The terms "driver" and "screwdriver" are used herein interchangeably to refer to a tool with a tip configured to engage the head of a screw or similar device, the tool being useful for rotating a screw or otherwise manipulating the screw, to drive a screw or, in this, case a cage into place in a joint. In some examples, a parallel spacer device may be used to space another guide pin in preparation for insertion of another cage. In some examples, a packing plunger assembly may be used to pack the cage with the above-mentioned materials. The packing plunger may be used to pack materials into the cage either or both pre- and post-insertion of the cage into the joint, and may be used with or without the tissue protector assembly.

Figure 1B:
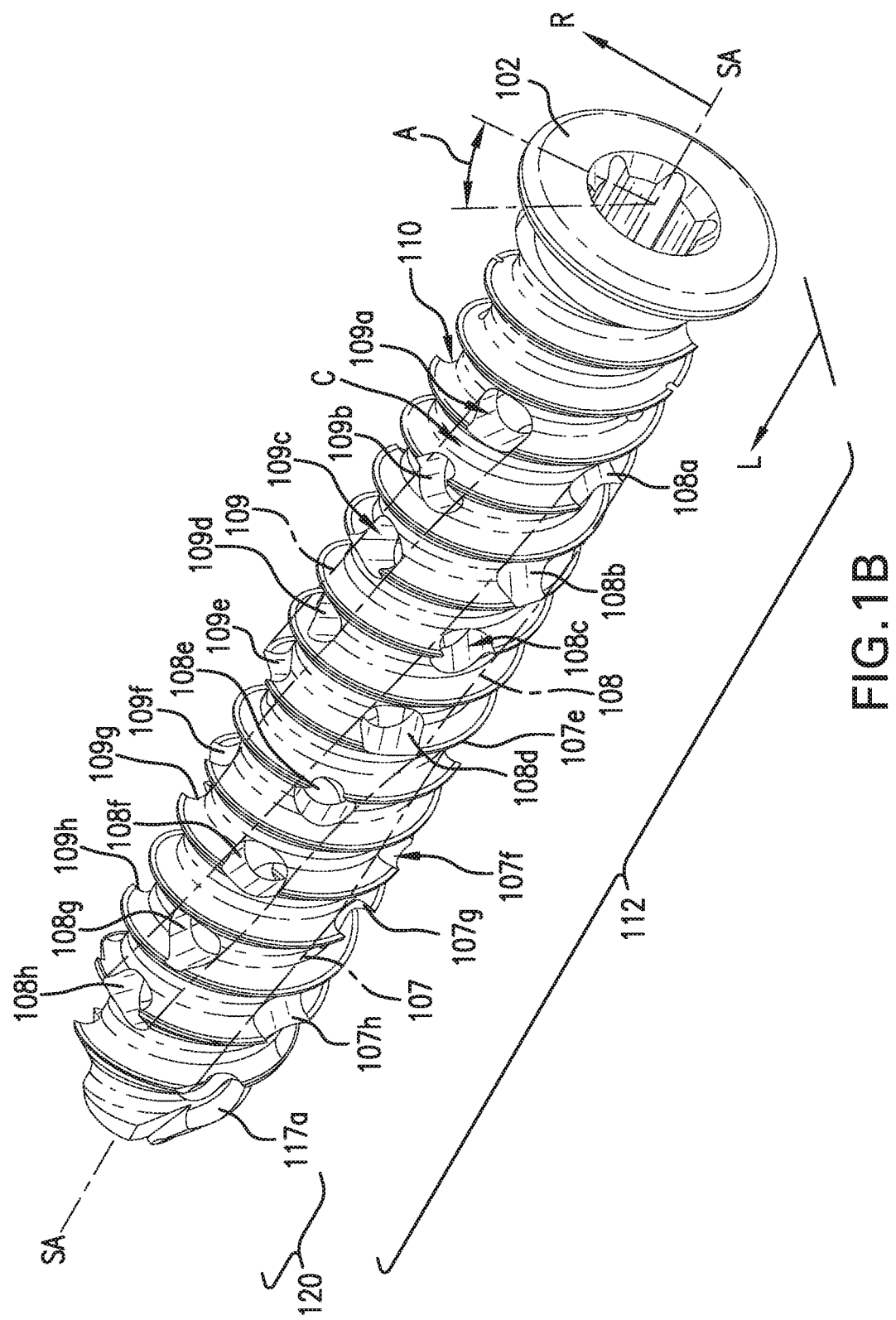
FIG. 1B is a perspective view thereof.
Figure 1C:
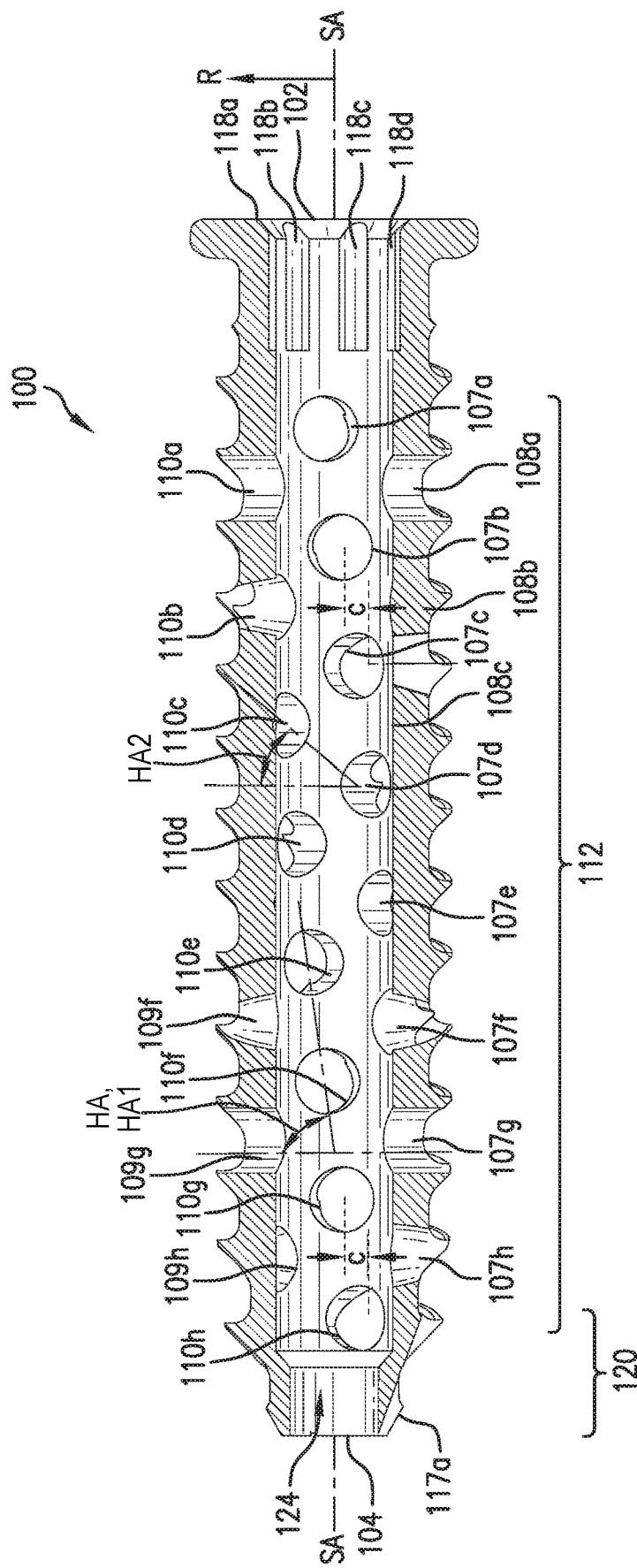
FIG. 1C is a cross-section view thereof.
Figure 1D:
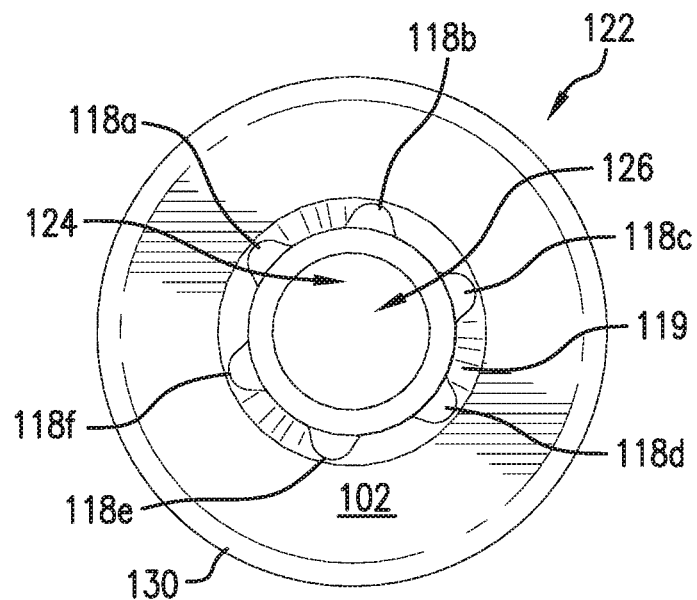
FIG. 1D is a proximal-end view thereof.
Figure 1E:
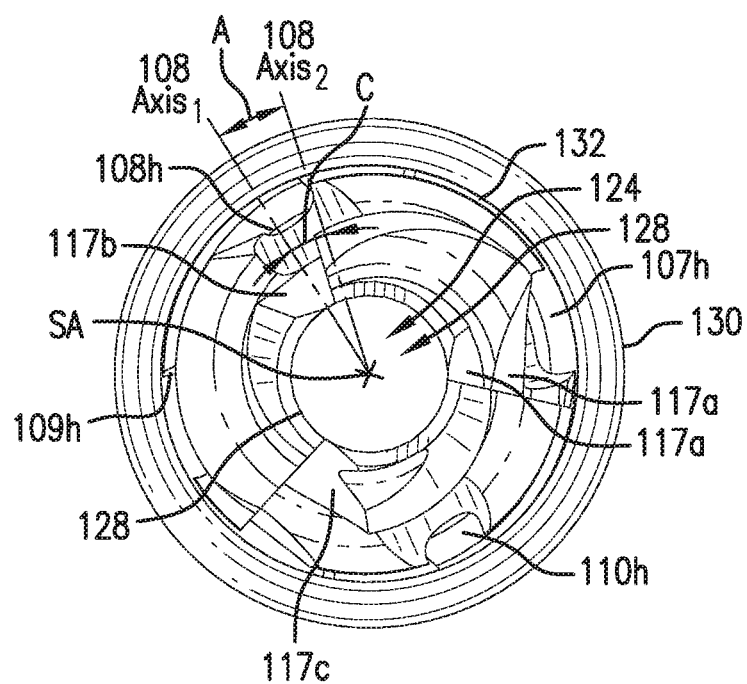
FIG. 1E is a distal-end view thereof.

FIGS. 1A-1C illustrate a side view, a perspective view, and a cross-section view, respectively, of an exemplary bone cage for joint fusion with end views shown in FIGS. 1D-1E. In accordance with various embodiments, cage 100 includes head 102, tip 104, one or more groups of helical fenestrations (e.g., fenestration groups 107-110), threads 112, and tapered end 120. Like-numbered and named elements in these views may describe the same or substantially similar elements. In some examples, cage 100 may be fabricated, manufactured, or otherwise formed, using various types of medical grade material, including stainless steel, plastic, composite materials, or alloys (e.g., Ti-6Al-4V ELI, another medical grade titanium alloy, or other medical grade alloy) that may be corrosion resistant and biocompatible (i.e., not having a toxic or injurious effect on tissue into which it is implanted). In some examples, threads 112 may be a helical ridge wrapped around an outer surface of cage 100's shaft. In some examples, cage 100 may be cannulated having a cannulated opening 124 formed by a hollow shaft that extends from head 102 to tip 104. Cage 100 may vary in length (e.g., ranging from approximately 25 mm to 50 mm, or longer or shorter) to accommodate size and geometric variance in a joint. Other dimensions of cage 100, including major 132 and minor 133 diameters of threads 112 (see, e.g., FIG. 1B), also may vary to accommodate size and geometric variance in a joint. In one example, head 102 may be 9.5 mm in diameter and threads 112 may have a major diameter 132 of 9 mm and a minor (i.e., root) diameter 133 of 7.4 mm. In other examples, head 102 may have a different diameter and threads 112 may have different major 132 and minor 133 diameters. In some examples, an outer surface of cage 100's shaft may taper from head 102 to tapered end 120, and thus threads 112 also may taper (i.e., be a tapered thread) from head 102 to tapered end 120 (e.g., having a range of major and minor diameters from head 102 to tapered end 120). In some examples, the tapering of threads 112, as well as tapered end 120, aids in guiding the cage through a pilot hole. In other examples, head 102 and threads 112 may be sized to fit within a tool or instrument, for example, a tissue protector 400, as described below.

In some examples, cage 100's hollow shaft, or cannula, may be accessed (i.e., for packing material into) through an opening 124 in head 102. In some examples, head 102 may have a flat or partially flat surface (e.g., pan-shaped with rounded edge, unevenly flat, or other partly flat surface). In other examples, head 102 may have a different shape (e.g., dome, button, round, truss, mushroom, countersunk, oval, raised, bugle, cheese, fillister, flanged, or other cage head shape). In some examples, the opening in head 102 may have a receiving apparatus for a torque applying tool such as driver. The driver may be flat head, Phillip's head, square head, hexagonal, head or any similar shape suitable to receive a tool and apply torque therefrom. In one example, the torque applying tool may be a driver having a TORX® or TORX®-like shape (i.e., six-point or six-lobed shape) (see FIG. 1D) configured to receive the tip of a TORX® or TORX®-like screwdriver (e.g., driver 902). For example, cage 100 may include head grooves 118a-118f which may start at head 102 and extend linearly into the cannula of cage 100 to receive complementary lobes on the end of a screwdriver. For a TORX® or TORX®-like opening there may be six (6) total head grooves, including, for example, head grooves 118a-118f, to receive the complementary lobes on the tip of a TORX® or TORX®-like driver. In some examples, as shown in FIG. 1C, the opening in head 102 may be contiguous with, and form a top end of, cage 100's cannula. For example, the opening may provide access to the cannula, for example, to pack material into the cage. The opening may also include a chamfer 119 providing a lead-in for a tool into the head grooves.

In accordance with various embodiments, the bone cage 100 has a length and a diameter forming an aspect ratio between the two. In various examples, the aspect ratio of the length to the diameter is greater than or equal to 5 to 1½. In one example, the aspect ratio of the length to the diameter is between 5 to 1½ and 3 to 2½. In one embodiment, the aspect ratio is 25 mm long to 9 mm diameter or about 2.7.

As described herein, the therapeutic materials may include osteogenic compounds (e.g., bone morphogenetic protein, or other osteogenic compounds that may ossify tissue), osteoconductive materials (e.g., demineralized bone, hydroxyapatite, or other material that promotes bone growth), antibiotics, steroids, contrast materials, or other materials that may be beneficial to fusing the joint, treating inflammation or other conditions in the joint, or enabling the visualization of the area within and adjacent to the cage. For example, an osteogenic compound, such as bone morphogenetic protein or other compounds, may be packed into cage 100's cannula such that when cage 100 is inserted into a joint or traverses through a joint (e.g., a sacroiliac joint), the osteogenic compound, for example through fenestrations (e.g., fenestrations 107a-107h, 108a-108h, 109a-109h, and/or 110a-110h), may come into contact with tissue in the joint adjacent to or surrounding cage 100, and ossify the tissue to fuse the joint across and through the cage. In some examples, the osteogenic compound may enter the joint and may fill the joint, partially or entirely. In other examples, an osteoconductive material, such as demineralized bone or hydroxyapatite or other materials may be packed into cage 100's cannula. When cage 100 is inserted into a joint (e.g., the joint between ilium I and sacrum S), the osteoconductive material may come into contact with tissue in the joint adjacent to or surrounding cage 100, for example through fenestrations (e.g., fenestrations 107a-107h, 108a-108h, 109a-109h, and/or 110a-110h), and promote bone growth into the cage and the joint to fuse the joint across and through the cage. In still other examples, a substance for treating sacroilitis, such as steroids or antibiotics or other substances, may be packed into cage 100's cannula such that when cage 100 is inserted into the joint, the substance may come into contact with tissue in the joint adjacent to or surrounding cage 100, for example through fenestrations (e.g., fenestrations 107a-107h, 108a-108h, 109a-109h, and/or 110a-110h), and treat the inflamed joint tissue. In yet other examples, a contrast material may be packed into cage 100's cannula such that, when cage 100 is inserted into the joint, the contrast material within cage 100, and in some examples absorbed by tissue adjacent to or surrounding cage 100, may be viewed using visualization techniques (e.g., x-ray, fluoroscope, ultrasound, or other visualization technique). In still other examples, different materials may be packed into cage 100 for different purposes. In yet other examples, the above-described materials may also come into contact with tissue adjacent to, or surrounding, cage 100 through an opening at tip 104. As described herein, cage 100 may be packed with material prior to being inserted into the joint, and may also be packed after insertion into the joint. Also as described herein, such materials may be packed into cage 100 using a packing plunger 1102 (see, e.g., FIG. 9).

In some examples, fenestrations (e.g., fenestrations 107a-107h, 108a-108h, 109a-109h, and/or 110a-110h) may provide therapeutic openings in cage 100's shaft to enable material packed inside cage 100 to come into contact with surrounding or adjacent tissue (e.g., bone, cartilage, or other tissue in the joint) when cage 100 is implanted. In various examples, the fenestration opening is 1 mm to 4 mm. In another example, the fenestration opening is 2 mm to 3 mm. In a preferred example, the fenestration opening is about 2½ mm. Additionally or alternatively, in various examples, the fenestrations (e.g., fenestrations 107a-107h, 108a-108h, 109a-109h, and/or 110a-110h) may be shaped to provide additional cutting edges or edges suitable to clean threads formed by the tip 120. In various examples, fenestrations (e.g., fenestrations 107a-107h, 108a-108h, 109a-109h, and/or 110a-110h) are substantially circular. In other examples, the fenestrations (e.g., fenestrations 107a-107h, 108a-108h, 109a-109h, and/or 110a-110h) are oblong (e.g., substantially oval, substantially elliptical, or other suitable shapes). In other examples, fenestrations (e.g., fenestrations 107a-107h, 108a-108h, 109a-109h, and/or 110a-110h) are shaped differently (e.g., rectangular, rounded rectangular, squared, triangular, or other suitable shapes).

In accordance with some embodiments, the bone cage 100 is manufactured by drilling fenestrations through the exterior of the device prior to cutting threads into the device. In this way, the location of the threads does not bias or effect the location of the fenestration in the bone cage 100. Additionally, the device can be free of other features such as grooves, slots or the like, that locate the fenestrations and tend to weaken the strength of the cage. In some examples, the fenestrations are consistently spaced with an omni-directional orientation or a generally omni-directional orientation that strengthens the cage 100.

In accordance with various embodiments, each cage may have an omni-directional orientation of the fenestrations along the cage length or across an individual section of the cage. An omni-directional orientation is one in which, along a fenestrated segment of a cage, a portion of the opening of the fenestrations are located across all radial directions of the cage. With the various openings of the fenestrations located in all radial directions, the cage can be implanted into the bone without regard to rotational alignment with the portion of the bone that is targeted for therapeutic treatment. Thus, in embodiments incorporating omni-directional orientation, a doctor does not need to orient the cage in the bone in order to optimize bone growth. The specific position of the holes can be located, in one example, in an organized manner (e.g., a pattern) or, in another example, they can be random. In various embodiments discussed in more detail below, the embodiments can include an omni-directional orientation. In other embodiments, the embodiments discussed herein can be formed without an omni-directional orientation. For example, along a set length of the fenestrated portion of the cage (i.e., the omni-directional segment length), e.g., 9 mm length of the cage, there is a portion of a fenestration opening in every radial direction. In various examples, a limited number of fenestrations are longitudinally aligned. For example, as shown in FIGS. 1A-C, fewer than three fenestrations have the same radial direction along the length of the cage or the segment. In one example, the cage has an omni-directional segment length that is approximately the same as the diameter of the cage. In another example, the omni-directional segment length is approximately the same as half the diameter of the cage. In another example, the omni-directional segment length is approximately the same as two times the diameter of the cage. In various examples, the omni-directional segment length is from about ½ the diameter of the cage to two times the diameter of the cage.

In accordance with various embodiments, each cage may have a generally omni-directional orientation of the fenestrations along the cage length or across an individual section of the cage. A generally omni-directional orientation is one in which, along a fenestrated segment of a cage, a portion of the opening of the fenestrations are located across substantially all radial directions of the cage. With the various openings of the fenestrations located in substantially all radial directions, the cage can be implanted into the bone with minimal regard to rotational alignment with the portion of the bone that is targeted for therapeutic treatment. Thus, in embodiments incorporating generally omni-directional orientation, a doctor has limited need to orient the cage in the bone in order to optimize bone growth. The specific position of the holes can be located, in one example, in an organized manner (e.g., a pattern) or, in another example, they can be random. In various examples, along a set length of the fenestrated portion of the cage (i.e., the generally omni-directional segment length), e.g., 9 mm length of the cage, there is a portion of a fenestration opening in substantially every radial direction. In various embodiments, the segment lengths for generally omni-directional orientation can be similar to the omni-directional orientation discussed above. Openings located in substantially all radial directions of the cage correspond to those that allow a doctor to place the screw without regard to the rotational orientation or alignment of the cage. Meaning, the therapeutic material is adequately delivered in each radial direction from the cage to the bone to achieve the goals of treatment regardless of the rotational orientation of the screw. In one example, fenestrations provide openings around 75-100% percent of the radial directions of the shaft but are distributed throughout the longitudinal length of the segment. In another example, the shaft includes longitudinal continuous strips of un-fenestrated portions that are present along the segment. The strips may have radial angles of less than 10°. In another example, the strips may have radial angles of less than 5°.

In accordance with some embodiments, the bone cage 100 is manufactured by drilling fenestrations through the exterior of the device prior to cutting threads into the device. In this way, the location of the threads does not bias or effect the location of the fenestration in the bone cage 100. Additionally, the device can be free of other features such as grooves, slots or the like, that locate the fenestrations and tend to weaken the strength of the cage. In some examples, the fenestrations are consistently spaced with an omni-directional orientation or a generally omni-directional orientation that strengthens the cage 100. The consistently spaced fenestrations allow for delivery of the therapeutic materials through the fenestrations to the bone in generally evenly distributed intervals. Generally evenly distributed intervals corresponds to intervals that allow sufficient therapeutic materials distribution to adequately treat the bone.

In accordance with various embodiments, each cage may have one or more helical rows of fenestrations. For example, second, third and fourth sets of fenestrations (e.g., fenestrations 107, 108, 109, 110) are disposed along a portion of the shaft from head 102 to tapered end 220, along the wall of cannula 224. In one example, these helical arrangements are omni-directional. Each different set of helical fenestrations is considered a new helical start. In one example, the starts can be tightly grouped together (e.g., two starts can be on the same half of the cylinder of the shaft) or alternatively, the starts can be uniformly spaced around the cylinder (e.g., two starts would be approximately 180° apart or four starts would be approximately 90° apart). In still other examples, each set of helically disposed fenestrations may include more or fewer fenestrations. In yet other examples, each set of fenestrations may be disposed at greater or lesser intervals. As illustrated in FIGS. 1A-1E and in some examples, cage 100 may include four helixes of fenestrations (e.g., fenestrations 107-110) disposed helically (i.e., in a helical row along a portion of the cage from head 102 to tapered end 120). For example, fenestrations 107 may be disposed helically along the cage 100, and fenestrations 108 may start along another side approximately 90° from fenestrations 107.

In accordance with various embodiments, the wall of the cage includes three or more helically positioned fenestrations or openings (e.g., at least three of any of fenestrations 107a-107h, 108a-108h, 109a-109h, and/or 110a-110h). The helix is defined by the position of the fenestrations relative to one another as the different fenestrations are variously located down some portion of the cage shaft from head 102 to tapered end 120, as shown by example in FIGS. 1A-1C. It should be noted that the helix is not defined by some abstraction in which various fenestrations can be connected by some envisioned abstract helix, but instead the fenestrations themselves clearly define the helix, as a person of ordinary skill in the art would recognize the various groupings of fenestrations as defining the shape and form of a helix.

The shape of the helix can be defined by the relative location and progression of each of the fenestrations along the shaft of the cage. These relative locations can be defined according to the longitudinal separation L and the angular separation A. The angular separation A between two adjacent fenestrations also corresponds to the circumferential gap between the two adjacent fenestrations. The overall helix can also be defined by the helix angle HA (see FIG. 1C) as measured from a plane or line perpendicular to the axis SA of the bone cage to the direction of the helix defined by the position of the fenestrations running along the bone cage. In some examples the helix angle is sufficiently large that the helix does not pass through the same fenestration twice. In accordance with various examples, the helix angle is greater than 15° and less than 90°. In one embodiment, the helix angle is steep being between about 45° and about 85° (see e.g. HA1). This angle allows for multiple helixes along the cage. In other embodiment, the helix angle is shallow being between about 15° and 45° (See e.g. HA2). In a preferred example, a single helix angle is about 28°. In another example, a cage has a double helix with helix angles that are about 40°. As used herein and illustrated in FIGS. 1A and 1B, the longitudinal separation L corresponds to the axial separation or distance between adjacent fenestrations in a helix along the axis SA of the cage 100. For example, the longitudinal separation of one fenestration relative to another is the axial distance between the centers (i.e., individual axes) of each of the fenestrations. As used herein and illustrated in FIGS. 1B and 1E, the angular separation A corresponds to the angle measured in the plane that is perpendicular to axis SA. For example, the angular separation A of one fenestration relative to another is the angle measured between a radius extending from axis SA through the center of one fenestration and a radius extending from axis SA through the center of an adjacent fenestration. FIG. 1E illustrates a particular example of the angular separation of fenestration 108h relative to fenestration 108g. Here fenestration 108h has an angular separation A relative to fenestration 108g. As shown in this example, angular separation A is measured between the axes 108A1 and 108A2 with the axes 108A1 and 108A2 being different axis R intersecting with axis SA. As used herein and illustrated in FIGS. 1B and 1E, the circumferential gap C corresponds to the circumferential separation that a first fenestration passes through the cage wall relative to the distance around the cage wall in which the adjacent fenestration in the helix passes through the cage wall. This is measured along the arc of the wall in a plane that is perpendicular to the axis SA. For example, the wall measured for the circumferential separation C may be the interior surface of the shaft that defines the cage cannula.

In accordance with various embodiments, there is cage shaft material that extends between adjacent fenestrations. As illustrated by way of example in FIG. 1A, bridges 111 connects fenestrations 109 (e.g., bridge 111a connects fenestration 109a to 109b), bridges 106 connects fenestrations 108, and bridge 105 connects fenestrations 107. While the bridges form part of the shaft as a whole, the bridge itself is in reference to the material directly between adjacent fenestrations. In accordance with various embodiments, the group of bridges (e.g., bridges 111a-111f) forming the shortest connection between adjacent fenestrations (e.g., 109a-109g) defines the helix (e.g., helix start 109).

In accordance with various embodiments, a helix on cage 100 is defined by a row of fenestrations (e.g., rows 107, 108, 109, or 110) in which adjacent fenestrations are separated from one another by a longitudinal separation L and an angular separation A. In various examples, each helix of fenestrations has a constant pattern where the longitudinal separation L and the angular separation A between adjacent fenestrations are constant along the length of the helix. In other examples the pattern is not constant but instead one or both of the angular separation A and the longitudinal separation L varies (increases or decreases) at a constant rate.

In accordance with various examples, the angular separation between adjacent fenestrations in a helix is greater than 0° such that a row of fenestration defines a helix as opposed to an axial line along the length of the cage 100. In one example, the angular separation is less than 120°. In one example, the angular separation is less than 90°. In one example, the angular separation is less than 60°. In one example, the angular separation is less than 45°. In one example, the angular separation is less than 20°. In one example, the angular separation is less than 10°. In a preferred example, the angular separation is between about 5° and 15°. In various examples, the angular separation from a first fenestration (e.g., 110a) proximal to the head 102 to a second fenestration (e.g., fenestration 110b) closer to the tip 104 is such that the helix defined by the fenestration wraps around the exterior of the cage 100 in the same direction as the threads 112. In some examples, the angular separation A between adjacent fenestrations is sized such that the lead (i.e., the axial advance of a helix during one complete turn around the circumference of the cage) of the fenestration helix is greater than the length of the cage.

In accordance with various embodiments, an angular segment of the cage 100 is an angle swept from a radial direction extending from the center line SA. This angular segment of the cage 100 may be considered a pie region of the cage 100. Each pie region may have about the same number of holes (e.g., within plus or minus one hole). For example, a 90° angular segment of the cage 100 can have 8-9 full fenestrations. In a preferred embodiment, the cage 100 includes 5 or more substantially equal angular segments with each of the angular segments having approximately the same number of fenestrations such that the cage 100 is operable to deliver therapeutic material in each direction of the angular segments in approximately the same amount or rate. In another embodiment, each angular segment has approximately the same cross sectional area of fenestrations such that the cage 100 is operable to deliver therapeutic material in approximately the same amount or rate.

In accordance with various examples, the longitudinal separation L between adjacent fenestrations in a helix is a distance greater than zero (0) such that a row of fenestration defines a helix as opposed to a circumferential line along the circumference of the cage 100. In one example, as illustrated in FIGS. 1A and 2B, the longitudinal separation L between adjacent fenestrations is greater than the pitch of the threads. In one example, the longitudinal separation L between adjacent fenestrations is less than the pitch of the threads. In one example, the longitudinal separation L between adjacent fenestrations is approximately the same as the pitch of the threads. In one example, as illustrated in FIG. 1A, the longitudinal separation L between adjacent fenestrations is approximately the same as or smaller than two times the diameter of the fenestration (e.g., the longitudinal separation of fenestration 110a relative to 110b is less than two times the diameter of fenestration 110a). In some examples, the longitudinal separation L between adjacent fenestrations is less than the diameter of the fenestration, but in such examples, the angular separation would be large enough as to form a bridge between fenestrations. In some examples, as illustrated in FIG. 2B, the longitudinal separation L between adjacent fenestrations is larger than two times the diameter of the fenestration. In some examples, the longitudinal separation L between adjacent fenestrations is large enough such that the lead (i.e., the axial advance of a helix during one complete turn around the circumference of the cage) of the fenestration helix is greater than the length of the cage.

The circumferential separation C of adjacent fenestrations is related to the angular separation A of the adjacent fenestrations based on the radius of the cage 100. For example, on two cages having different diameters but with adjacent fenestrations having the same angular separation A, the larger cage will have a larger circumferential separation C proportional with the increase in radius size of the cage compared to the smaller diameter cage. In accordance with various examples, the circumferential separation between adjacent fenestrations in a helix is greater than zero (0) such that a row of fenestration defines a helix as opposed to an axial line along the length of the cage 100. In accordance with various examples, the circumferential separation C between adjacent fenestrations in a helix is less than the diameter of the fenestration. In various examples, the circumferential separation C between adjacent fenestrations in a helix is less than half the diameter of the fenestration. In a preferred example, the circumferential separation C between adjacent fenestrations in a helix is between about one-tenth (1/10) and one-third (1/3) of the diameter of the fenestration. In some examples, the circumferential separation C between adjacent fenestrations in a helix is greater than the diameter of the fenestration and less than half the circumference of the cage 100.

In accordance with various embodiments, each adjacent fenestration may have a helically extending bridge of material extending therebetween, as discussed above. In some embodiments, the length of the bridge is greater than the thread pitch. In other embodiments, the length of the bridge is less than the thread pitch. In other embodiments, the length of the bridge is less than the diameter of the fenestration. In other examples, the length of the bridge is greater than the diameter of the fenestration. In various examples, the length of the bridge wraps less than a third of the way around the cage. In various examples, the length of the bridge wraps less than a quarter of the way around the cage.

In accordance with a preferred embodiment, as illustrated in FIG. 1C, the length of the bridge wraps between one-sixty-fourth (1/64) and one-sixteenth (1/16) of the way around the cage 100.

In accordance with various embodiments, the helix of fenestration on cage 100 may include any suitable combination of the examples of the longitudinal separation, the circumferential separation, the angular separation and/or the bridge configurations discussed herein. As discussed herein, each cage 100 can include multiple helixes (i.e., multiple starts to each helix). Each helix can include any suitable combination of the examples of the longitudinal separation, the circumferential separation, the angular separation and/or the bridge configurations discussed herein. In some embodiments, each helix is parallel to the adjacent helixes. In other embodiments, one or more of the helixes has a different profile or characteristics as opposed to the other helixes of fenestrations on the cage 100. In various examples, the fenestrations in adjacent helixes do not align longitudinally (i.e., axially) with the fenestrations of the next helix. Such a configuration can allow for a fenestration opening to be located along the entire length of the cage 100 with each opening located at a different point around the circumference of the cage.

In accordance with the various embodiments, some or all of the fenestrations form openings from the profile of the thread into the cannula. The fenestration openings from the exterior of the cage 100 to the interior cannula 124 are defined by generally radially extending passages. In one embodiment the passages are formed as a steep bore with straight cross sectional walls that extend from the thread profile to the cannula. The surface defining the bore from the thread profile to the cannula extends in the generally radial direction. For example, the fenestration may avoid any surfaces or features other than the thread profile that is not radially extending from the cannula to the exterior of the cage 100. Meaning the fenestration avoids any surfaces tangential to the circumference of the cage and/or is generally absent a surface that faces in a generally outward direction from the cage. In accordance with the various embodiments, some or all of the fenestrations form openings directly through a natural portion of the thread. As used herein, the natural portion of the thread 112 includes an uninterrupted profile of the thread. Examples of interruptions in the thread include grooves, slots, flats, shelves or other features machined, molded, cut, or otherwise formed into the threads, that are not actually part of the thread itself but serve another purpose than advancing the cage through the bone. Stated another way, at least some of the fenestrations in each helix discussed above, avoid extending through any grooves, slots, flats, shelves or other features machined, molded, cut, or otherwise formed into the threads, that are not actually part of the thread itself but serve another purpose than advancing the cage through the bone. While in some embodiments, some of the fenestrations may intersect thread interruptions or similar features, in such embodiments, some of the fenestrations can still avoid such intersections allowing the helix to still be defined by those fenestrations that avoid such intersections. By having the fenestrations intersect the threads directly, injected material is permitted to flow around and through the outside of the bone screw, and not just into areas contacting the minor diameter of the screw. In some embodiments, the cage may have multiple leads (e.g. dual starts). As such, the injected material can create two discrete helical sections as it escapes the threads through the fenestrations. By having the fenestrations break through the thread profile, it enables adjacent thread areas (e.g. the two separate thread helixes) to be contacted by a continuum of the injected media. Additionally, by forming the threads such that the fenestrations pass directly through the threads forming a self-tapping feature having sharp edges that cut into the bone while being threaded into place. In accordance with various embodiments, the threads have a crest that is rounded or peaked (e.g. having a point comparable to the root of the thread). In other embodiments, the thread may have a flattened crest.

By having the fenestrations open directly through the otherwise uninterrupted thread profile, the exterior fenestration openings open directly to the bone that supports the threads 112 inside of the ilium I, sacrum S, or the joint there between. Thus, when therapeutic material is delivered to the bones through the fenestrations (e.g., fenestrations 107-110) along the cage 100, it is delivered at discrete locations directly to the bone helically along the length of the cage, thus avoiding flow of material into thread interruptions and away from the targeted discrete locations. Also this maintains the cage thread profile along the length of the cage except in the discrete locations of the fenestrations.

In accordance with various embodiments, the fenestrations extend from the cannula 124 to the exterior of the cage 100 with groups of fenestrations forming helical paths (e.g., 107, 108, 109, and 110.) The various fenestrations are positioned on the cage and as the cage threads contact the bone structure directly when implanted, the various openings of each of the individual fenestrations open directly onto the bone structure in both major diameters (the peaks) and minor diameters (the valleys of bone structure formed by the threads of the cage. The various openings forming the fenestrations also open directly onto the bone and form helical patterns along the length of the cage such that therapeutic material is delivered to the bone structure directly from the fenestration openings and to the bone in helically arranged discrete locations corresponding to the locations of the various fenestrations.

In various embodiments, the fenestration helixes do not follow the thread helix. In some examples of this, the thread helix has a period that is different and also not a multiple of the fenestration helixes such that the fenestration helixes vary in how they pass through the thread profile, sometimes passing through and centered on the minor diameter of the thread, sometimes passing through and centered on the major diameter, and sometimes centered in between the major and minor diameters.

Figure 2A:
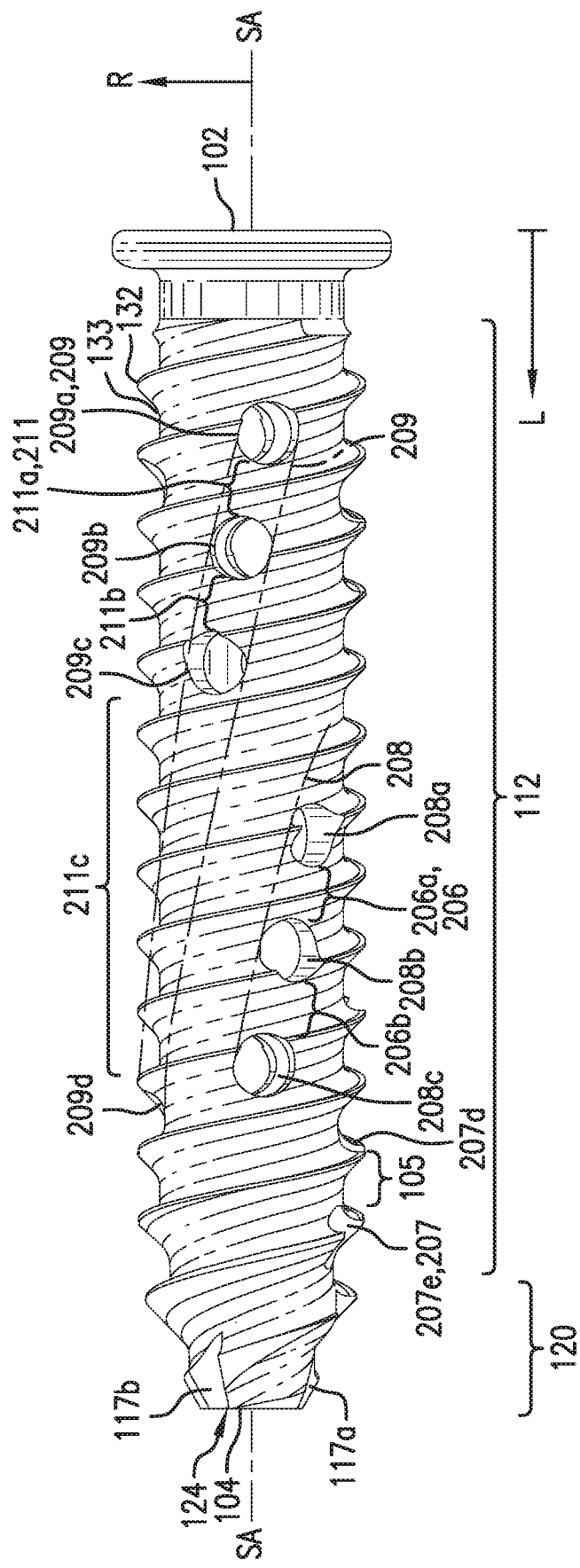
FIGS. 2A and 2B are side views of cages for joint fusion according to alternative embodiments.
Figure 2B:
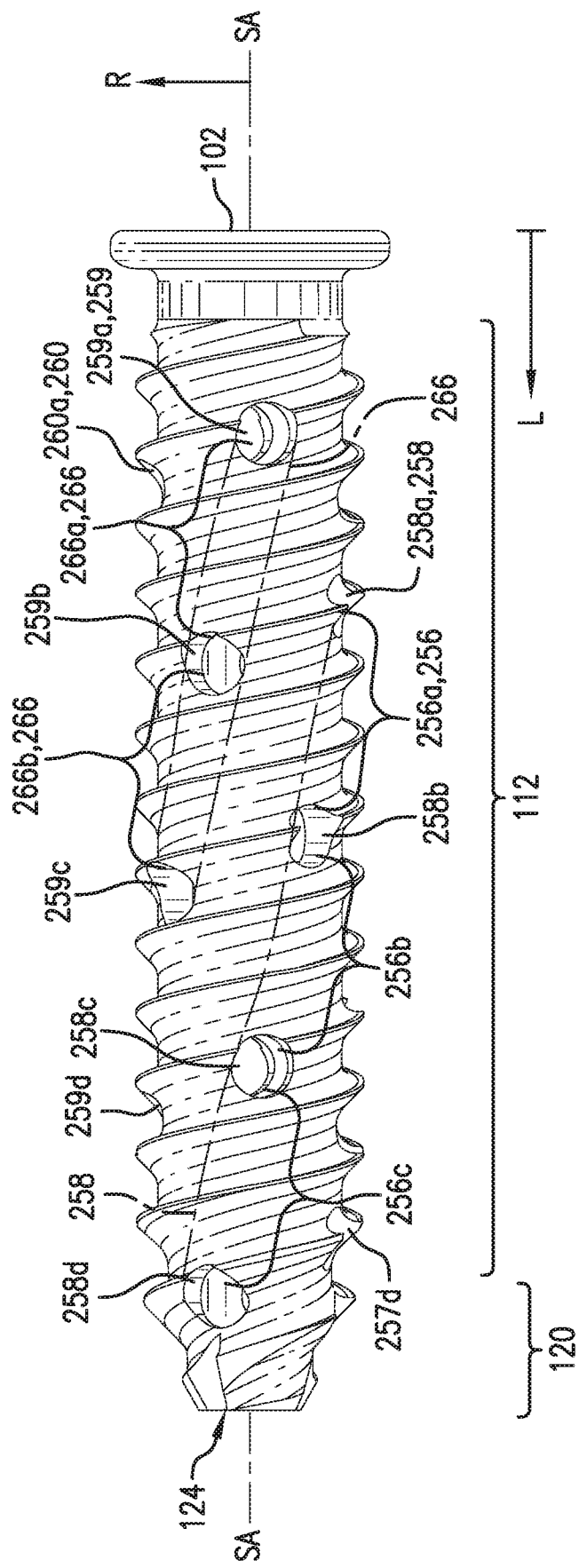

FIGS. 2A-2B illustrates side views of alternative exemplary cages for joint fusion. Here, cage 100 includes head 102, tip 104, fenestrations, threads 112, shaft grooves 114 and tapered end 120. Like-numbered and named elements in these views may describe the same or substantially similar elements above. For example, like-named elements in FIGS. 2A-2B may describe the same or substantially similar elements at those in FIGS. 1A-1E. Elements with different numerical identifies refer to elements that are substantially different from the embodiments of FIGS. 1A-1E (e.g., the fenestrations). In various embodiments, the various elements (e.g., threads, fenestrations, cannula, etc.) of the cage 100 may have one or more of the various characteristics or combinations of characteristics discussed above with regards to FIGS. 1A-1E. FIG. 2A shows an example of a cage having groups of fenestrations. For example, helix 208 of fenestrations 208a, 208b, and 208c (with bridges 206a and 206b there between) occupy less than half the length of the cage 100. In another example, helix 109 of fenestrations 209a, 209b, 209c, and 209d, illustrate a variation in the spacing of the fenestrations as discussed in more detail below. FIG. 2B, as discussed above, illustrates, an alternative example of fenestrations (e.g., fenestrations 260a, 259a-259c, and 258a-258d along with bridges 266a-266b and 256a-256c)) on the same respective helixes (260, 259, and 258) with a lower frequency than shown in FIGS. 1A-1E.

As shown in the examples illustrated in FIGS. 1A-1E, the respective angular separation between adjacent fenestration is constant along the length of the cage and/or the length of the helix. Similarly, FIG. 2B illustrates helixes in which the respective angular separation between adjacent fenestration is constant. FIG. 2A on the other hand illustrates an example having helixes (e.g., 209) in which the respective angular separation between adjacent fenestration is not constant. A variable angular separation is one in which, the angular separation between two adjacent fenestrations in a helix is different that the angular separation between two other adjacent fenestrations in the helix. For example, fenestrations 209a, 209b, 209c, and 209d are all in the same helix. However, the angular separation between fenestrations 209b and 209c is different than the angular separation between fenestrations 209c and 209d. The variations in the angular separations may form a pattern. The variations may be progressively larger. In some embodiments, they may be progressively smaller. In other embodiments, they may increase and then decrease. In other embodiments, they may be irregular in the way they change along the helix(es). In some embodiments, there may be a single variation, and in other there may be multiple variations.

As shown in the examples illustrated in FIGS. 1A-1E, the longitudinal separation between adjacent fenestration is constant along the length of the cage and/or the length of the helix. Similarly, FIG. 2B illustrates helixes in which the longitudinal separation between adjacent fenestration is constant. FIG. 2A, on the other hand, illustrates an embodiment having helixes (e.g., fenestrations 209) in which the respective circumferential separation, longitudinal separation, or combined helical separation between adjacent fenestrations is not constant. A variable longitudinal separation is one in which the longitudinal separation between two adjacent fenestrations in a helix is different that the longitudinal separation between two other adjacent fenestrations in the helix. For example, fenestrations 209a, 209b, 209c, and 209d are all in the same helix. However, the longitudinal separation between fenestrations 209b and 209c is different than the longitudinal separation between fenestrations 209c and 209d. The variations in the longitudinal separations may form a pattern. The variations may be progressively larger. They may be progressively smaller. They may increase and then decrease. They may be random in the way they change. In some examples there may be a single variation, in other examples there may be multiple variations. Such variations are selected so that they still result in the adjacent fenestrations remaining on the same helix, because as the longitudinal separation may change, the angular or circumferential separation may proportionally change to maintain a helical relationship between fenestrations.

In accordance with various embodiments, each adjacent fenestration may have a bridge of material extending therebetween, as discussed above. In various examples the length of the bridge can change. For example, as shown in FIG. 2A, the bridge 211b is a smaller length than the next adjacent bridge down the length of the cage bridge 211c. In accordance with various embodiments, the helix of fenestration on cage 100 may include any suitable combination of the elements or characteristics of the longitudinal separation, the circumferential separation, the angular separation and/or the bridge configurations in the various examples discussed herein (e.g., examples shown in FIGS. 1A-1E or 2A-2B or any discussed above).

In some examples, tip 104 may be disposed on tapered end 120. In some examples, tip 104 may provide another opening for material packed inside the shaft to come into contact with surrounding or adjacent tissue. In some examples, this opening may be circular, with the same or similar diameter as the cannula of cage 100. In other examples, the opening may be smaller in diameter than the cannula of cage 100. In some examples, the opening in tip 104 may be contiguous with, and form an end of, cage 100's cannula. In some examples, tapered end 120 may aid in guiding cage 100 into a pilot hole. In various embodiments the tip begins to form threads (i.e., tap threads) into the predrilled hole. The tip includes one or more flutes (e.g., flutes 117a-c) extending through the threads. The flutes cut through the threads but not the wall defining the cannula 124.

In some examples, openings in cage 100, including fenestrations (e.g., fenestrations 107a-107h, 108a-108h, 109a-109h, and/or 110a-110h), and tip 104, may enable cage 100 to deliver materials to bone and other joint tissue adjacent to, or surrounding, cage 100, for example, to regenerate bone or treat inflammation, infection, or other ailments, in the joint. For example, cage 100 may have a cannula in which such materials may be packed, as described herein. After being packed, cage 100 may be implanted (i.e., inserted) into or across a joint, and such therapeutic materials may be delivered from cage 100 through fenestrations (e.g., fenestrations 107a-107h, 108a-108h, 109a-109h, and/or 110a-110h) or other openings (e.g., in head 102 or tip 104 of cage 100) and to a joint. In some examples, the above-described materials may fill a joint, partially or entirely, after entering the joint through fenestrations (e.g., fenestrations 107a-107h, 108a-108h, 109a-109h, and/or 110a-110h).

FIG. 1D illustrates a top view of an exemplary cage for joint fusion. In accordance with various examples, such as those illustrated in FIG. 1D, end 122 includes head 102, shaft 124, openings 126, 128, head grooves 118a-118f and head diameter 130. Like-numbered and named elements in these views may describe the same or substantially similar elements above. In some examples, head 102 may be circular with head diameter 130. In some examples, head diameter 130 corresponds to the diameter of a cannula of a tissue protector (e.g., tissue protector 404). In other embodiments, head 102 may be shaped differently (e.g., triangular, hexagonal, or other shapes not shown). In some examples, opening 126 may be disposed at head 102, and opening 128 may be disposed at tip 104 (see e.g., FIG. 1E). In some examples, the diameters of openings 126 and 128 may be the same or similar. In other examples, the diameter of openings 126 may be different from the diameter of opening 128.

In some examples, cannula 124 may extend uninterrupted from head 102 to tip 104. In some examples, cannula 124 may be configured to fit over a guide pin, as described herein. In some examples, cannula 124 also may be configured to receive and hold material (e.g., osteogenic compounds, osteoconductive materials, antibiotics, steroids, contrast materials, or other materials that may beneficial to fusing the joint, treating inflammation or other conditions in the joint, or enabling the visualization of the area within and adjacent to the cage, as described herein).

FIG. 1E illustrates a bottom view of an exemplary cage for joint fusion. In accordance with various embodiments, bottom end includes tip 104, fenestrations (e.g., one or more of 107h, 108h, 109h, 110h) tapered end 120, cannula 124, opening 128, head diameter 130 and major diameter 132. Like-numbered and named elements in these views may describe the same or substantially similar elements above. In some examples, opening 128 are disposed at tip 104 and the end of cannula 124. In some examples, head diameter 130 may be larger than major diameter 132. In various examples, major diameter 132 in turn may be larger than a minor 133 (i.e., root) diameter.

In some examples, cages 100 (e.g., shown in FIGS. 1A-1E or FIGS. 2A-2B) can be configured to fit or slide within a tissue protector (e.g., tissue protector 404) and/or over a guide pin (e.g., guide pin 418) into a joint. In other examples, cages 100 may be formed differently and are not limited to the examples described.

Figure 3:
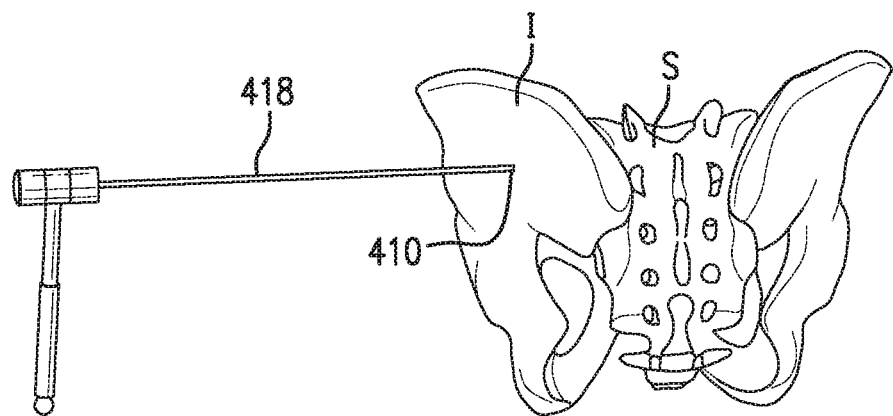
FIG. 3 illustrates a guide pin being set in a sacroiliac joint according to one embodiment of a surgical procedure for joint fusion.

FIG. 3 illustrates an exemplary guide pin 418. In some examples, guide pin 418 may be a medical grade sterile metal pin (e.g., Kirschner wire, Steinmann pin, or other metal pin) suitable for use in medical procedures. In some examples, guide pin 418 may be used for alignment and guidance of a tissue protector (e.g., tissue protector 404), an implant (e.g., a cage or other implant), and other tools into the ilium I, the sacrum S or the joint there between. The guide pin 418 can be set into the patient via twisting, hammering, pressure or any other suitable method. In a particular example, mallet 417 drives the guide pin 418 into the ilium and/or the sacrum. In some examples, guide pin tip 410 may form a trocar for introducing tissue protector assembly 400 into a bone.

Figure 4A:
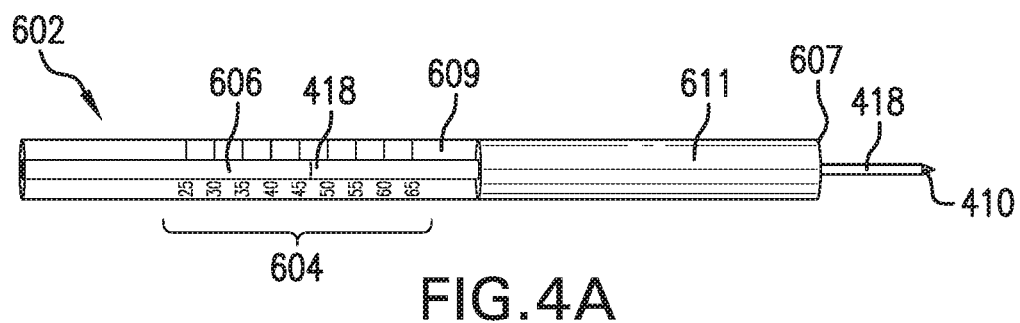
FIG. 4A illustrates a depth gauge according to one embodiment for determining the depth of a pilot hole to be drilled for insertion of a cage for joint fusion.
Figure 4B:
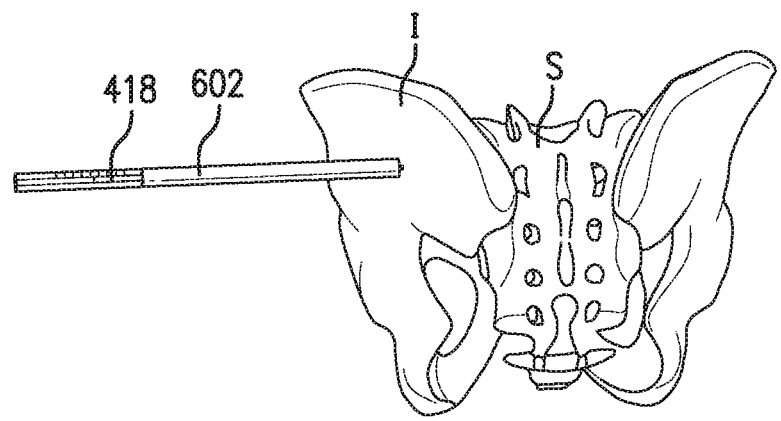
FIG. 4B is a view thereof installed over a guide pin being set in a sacroiliac joint in the procedure of FIG. 3.

FIG. 4A illustrates an embodiment of a depth gauge 602 for determining the depth of a guide pin to be inserted into the ilium I and/or sacrum S. In various embodiments, depth gauge 602 includes depth markings 604, channel 606, and distal contact surface 607. In various examples, the channel 606 is formed along an exposed wall 609 of the depth gage. The channel 606 transitions into an enclosed channel through a lower body portion 611. The contact surface 607 is located on the distal end of the lower body portion 611 and is suitable to contact the ilium I. The guide pin 418 may then be slid into the depth gauge 602 to the desired depth as measured on the depth markings 604. In some examples, depth gauge 602 may be configured to determine the depth in which guide pin 418 is inserted into a bone and/or joint. In some examples, depth gauge 602 may include depth markings 604, which can measure the depth in which the guide pin 418 is driven into the ilium. In some examples, depth markings 604 may indicate a range of 25-65 mm depths. In other examples, depth gauge 602 may have different depth markings, and thus indicate a different range of depths. The number in depth markings 604 that corresponds to the location of the end of guide pin 418 may indicate the depth of guide pin 418. In other examples, depth markings 604 can indicate a different depth that may correspond and be calibrated to the depth of guide pin 418 (e.g., depth markings 604 may indicate a desired drilling depth for a pilot hole, a depth of a cage to be implanted, or other depth that is associated with the depth of guide pin 418, and may thus be measured against the depth of guide pin 418). In still other examples, depth gauge 602 may include more or fewer elements and is not limited to the examples described.

Figure 5A:
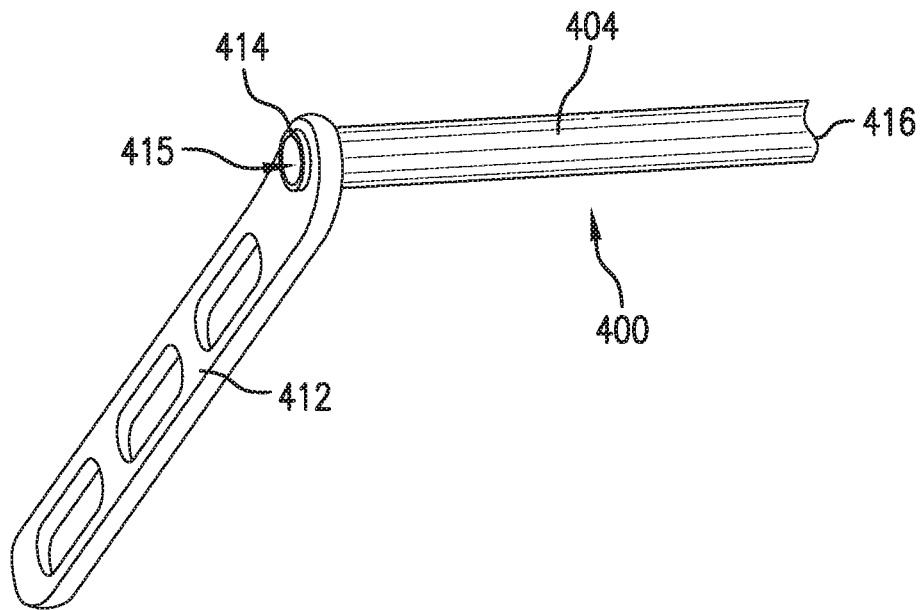
FIG. 5A illustrates a tissue protector according to one embodiment.
Figure 5B:
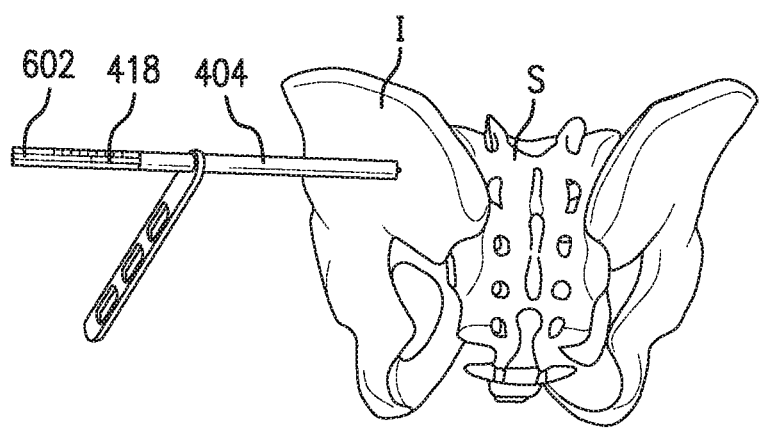
FIG. 5B is a view thereof placed over a guide pin and set in a sacroiliac joint in the procedure of FIG. 3.

FIGS. 5A and 5B illustrate a tissue protector assembly 400. The tissue protector assembly may include sleeve 404 and handle 412. In some examples, tissue protector sleeve 404 may include a tissue protector head 414, and tissue protector tip 416. In some examples, sleeve 404 has a hollow shaft 415 having a close fit to one or more of the depth gauge 602, the cage 100, and or a drill 700. In some embodiments, the guide pin 481 may be utilized with a guide pin sleeve. The guide pin sleeve can receive into the guide pin sleeve. The guide pin sleeve can then be inserted into the tissue protector. In various embodiments, the guide pin sleeve includes a close tolerance to the interior of the channel 415 of the tissue protector so that the guide pin is accurately positioned in the tissue protector 404. In some embodiments, the guide pin 418 is centered in the tissue protector 400. In other embodiments, the depth gauge 602 functions as the guide sleeve. In some examples, the outer diameter of pin sleeve (e.g., depth gauge 602) shaft is shaped to fit inside the cannula of tissue protector 400, which has an internal diameter that may be configured to accommodate tools and implants (e.g., cages 100, and the like) having a larger diameter than a guide pin. For example, the diameter of tissue protector 404's cannula 415 may correspond to (i.e., be sized to fit) the head or outer diameter on an implant (e.g., cages 100). In some examples, the internal surface of tissue protector 400 may be configured to guide an implant (e.g., cage 100) inserted into tissue protector 400 from tissue protector head 414 and through to tissue protector tip 416.

In some examples, tissue protector tip 416 may have spikes, teeth, wedges, or other structures, to engage a bone. As shown, tissue protector tip 416 is engaged with an ilium (i.e., its spikes, teeth, wedges or other structure for engaging a bone, are embedded in the ilium). In some embodiments, the tissue protector tip 416 does not embed into the bone but merely increases friction such that the tissue protector tip 416 does not slip on the exterior of the bone. In other examples, tissue protector assembly 400 may be formed differently and is not limited to the examples described.

FIG. 5B illustrates an exemplary tissue protector assembly placed over a guide pin. Here, diagram 420 may include tissue protector sleeve 404, handle 412, tissue protector head 414, tissue protector tip 416 and guide pin 418 and depth gage 602 (functioning as a guide pin sleeve). Like-numbered and named elements in this view may describe the same or substantially similar elements as in previous views (e.g., FIG. 4A).

Figure 6A:
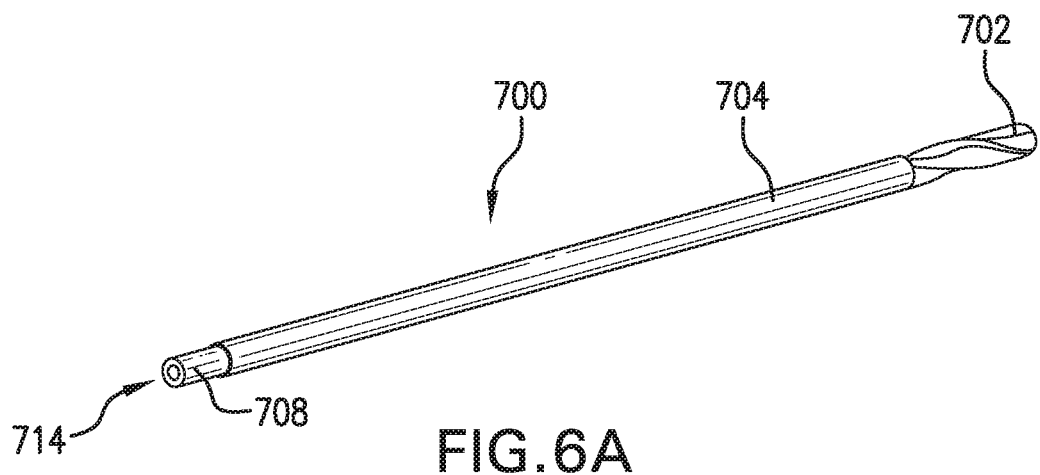
FIG. 6A is a perspective view of a cannulated drill bit for drilling a pilot hole for insertion of a cage for joint fusion according to one embodiment.
Figure 6B:
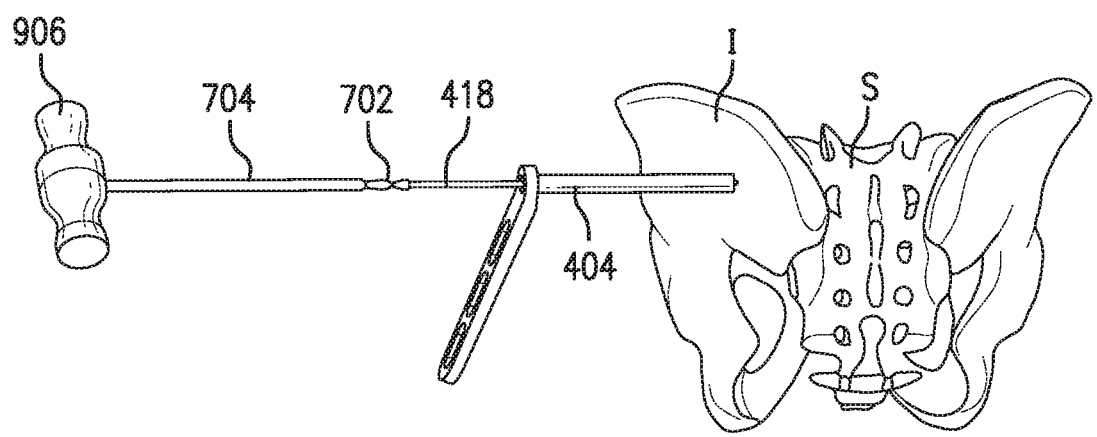
FIG. 6B is a side view thereof being placed over the guide pin for drilling a pilot hole for insertion of a cage for joint fusion in the procedure of FIG. 3.

FIGS. 6A and 6B illustrates a side view of an exemplary cannulated drill bit and for drilling a pilot hole for insertion of a cage for joint fusion. Here, cannulated drill bit 700 may include cutting tip 702, body 704, and shank 709. As used herein, "drill bit" refers to any cutting tool configured to create substantially cylindrical holes, and "shank" refers to an end of the drill bit, usually the end opposite the cutting tip, configured to be grasped by a chuck of a drill, handle or other torque applying device. In some examples, cannulated drill bit 700 may be configured to drill a pilot hole to a predetermined depth. For example, cutting tip 702 may be configured to cut cylindrical holes into a bone and/or joint when torque and axial force is applied to rotate cutting tip 702 (i.e., by a drill). In some examples, cannulated drill bit 700 may be adjustable, and thereby configured to drill a range of depths using depth markings. The outside diameter of cannulated drill bit 700 may be configured to fit within a tissue protector (e.g., tissue protector 400). In some examples, the outside diameter may be significantly smaller than the tissue protector 400, such that the tissue protector does not provide significant support to the drill bit 700 or function as the primary locating tool for the drill bit 700. In other examples, the tissue protector 400 may function as the drill guide, providing significant support and locating functionality to the drill bit 700 by having an inner diameter that is substantially the same size as the outer diameter of the drill bit 700. The variance in sizes being sufficient to allow the drill bit 700 to slide and rotate within the tissue protector.

In some examples, a desired drilling depth (i.e., depth of a pilot hole) may be the same or similar to the depth of a guide pin that has been inserted into a bone and/or joint. In other examples, the desired drilling depth may be offset (i.e., less deep) by a predetermined amount (e.g., a few millimeters or other offset amount). For example, if a guide pin has been inserted 40 mm deep into the sacroiliac joint, a corresponding desired drilling depth for the pilot hole may be 40 mm, or it may be 40 mm minus the predetermined offset may be selected (i.e., if the predetermined offset is 3 mm, then the desired drilling depth in this example would be 37 mm).

The cannulated drill bit 700 includes cannula 714. In some examples, cannula 714 are sized to fit over a guide pin (e.g., guide pin 418). A driver handle 906 may receive the shank 709 allowing a user to apply a torque to the drill bit 700. The drill bit 700 may be slid down over the guide wire 418 thereby accurately locating the drill bit 700 based on the insertion location of the guide wire 418 into the bone. Tissue protector 400, particularly the sleeve 404 thereof protects the tissue surrounding the drill site from being damaged by the drilling action. The drill may than form hole through one or more bones (e.g., ilium I and/or Sacrum S).

Figure 7A:
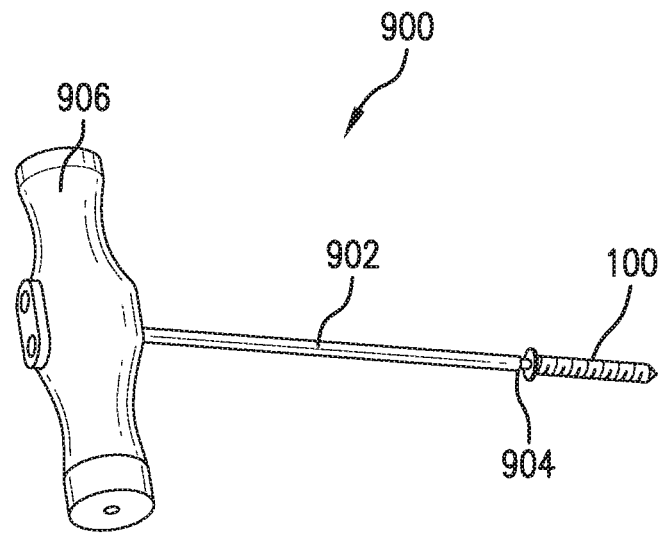
FIG. 7A is a perspective view of a driver for driving a bone cage for insertion of the cage for joint fusion according to one embodiment and FIG. 7B is a side view thereof driving a bone cage into a joint for fusion in the procedure of FIG. 3.
Figure 7B:
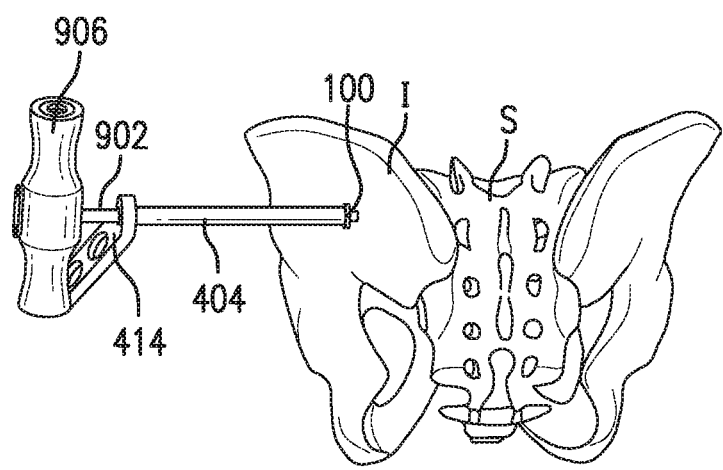

FIGS. 7A and 7B illustrate an exemplary driver 902 for inserting a cage 100 for joint fusion. Driver assembly 900 includes driver 902, mating tip 904, driver handle 906, tissue protector 404, handle 412, and tissue protector head 414. In some examples, driver 902 may be configured to drive a cage (e.g., cages 100) into a bone and/or joint. In some examples, driver 902 may have a shaft configured to fit or slide within tissue protector 404. In some examples, mating tip 904 may be shaped to engage (i.e., fit) a head of a cage (e.g., head 102). For example, driver 902 may be a TORX® driver and mating tip 904 may be shaped to fit a TORX® head cage (e.g., with a six-point or six-lobed shape). In other examples, mating tip 904 may be shaped differently to engage suitable types of cages (e.g., PHILLIPS™ (i.e., having a cruciform or cross shape with four lobes), slot, flat, Robertson, hex, or other type of cages). In some examples, driver handle 906 may be used to turn driver 902, and consequently turn a cage engaged by mating tip 904. In some examples, driver 902 may be a manual driver. In other examples, driver 902 may be powered (i.e., electrically). In some examples, driver 902 also may be ratcheting or torque-limited. In some examples, driver handle 906 may be formed separately from driver 902's shaft and driver tip 904. In some examples, handle 906 may be configured to be removably coupled with various types of drivers (e.g., TORX®, PHILLIPS™, slot, flat, Robertson, hex, or other types of cage drivers). In other examples, driver 902 and driver handle 906 may be formed differently, and are not limited to the examples shown and described. The cage 100 includes a cannula that slides over the guide wire 418 and into tissue protector sleeve 404. The driver 902 forces the cage 100 down sleeve 404 until contact is made with the bone. Then a torque is applied to cage 100 by the handle 906 causing the cage to twist into the bone.

Figure 8:
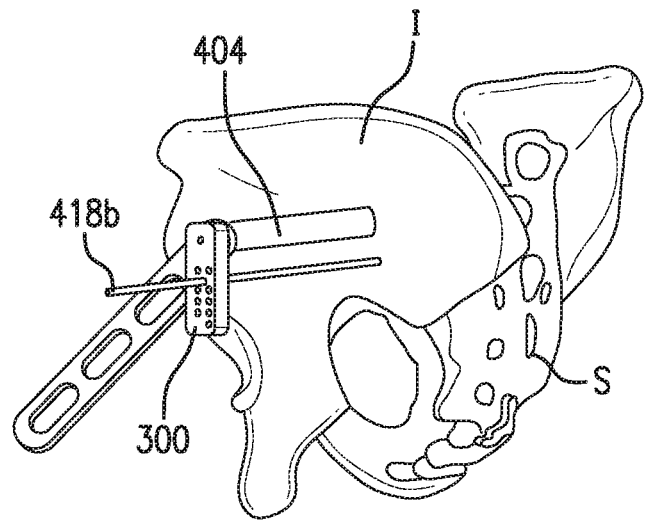
FIG. 8 is a perspective view of a parallel guide according to one embodiment being used to set a guide pin at a new location in a sacroiliac joint in the procedure of FIG. 3.
Figure 9:
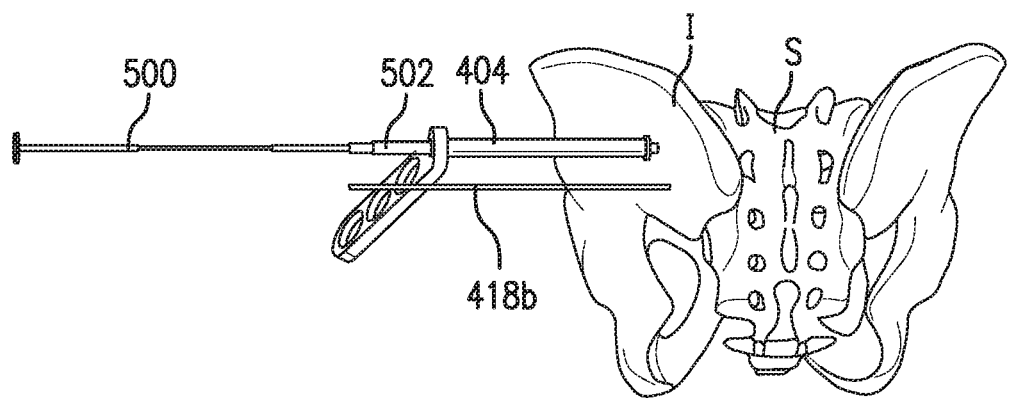
FIG. 9 illustrates a packing plunger assembly according to one embodiment placed in a tissue protector assembly for packing a cage for joint fusion in the procedure of FIG. 3.

FIG. 8 illustrates a side view of an exemplary parallel spacer instrument 300 for placement of another guide pin 418*b*. FIG. 9 illustrates a second pin placed parallel to the first setup. This is accomplished by running the additional pin 418*b* through the spacer block as shown in FIG. 8. In some examples, guide pin 418 may still be in place within tissue protector 400. Once the parallel spacer instrument 300 is placed on tissue protector 400, a next guide pin 418*b* is inserted through the parallel spacer reaching down to engage the bone (e.g., an ilium).

FIG. 9 illustrates a perspective view of an exemplary packing plunger 500 placed in a dispensing tube 502. In some examples, dispensing tube 502 and plunger 500 work together to dispense therapeutic material into the cage located in the bone (e.g., ilium and/or sacrum). The plunger and the dispensing tube dispense various therapeutic materials (e.g., liquids, gases, gels, or other materials. As described herein, such therapeutic materials include osteogenic compounds (e.g., bone morphogenetic protein, or other osteogenic compounds that may ossify tissue in the joint), osteoconductive materials (e.g., demineralized bone, hydroxyapatite, or other material that promotes bone growth), antibiotics, steroids, contrast materials, or other materials that may beneficial to fusing the joint, treating inflammation or other conditions in the joint, or enabling the visualization of the area within and adjacent to the cage. In some examples, plunger 500 may be depressed to dispense material from dispensing tube 502, for example, into a cannulated cage (e.g., cages 100), which may in turn deliver said material into a joint, as described above, through the fenestrations discussed above.

Although the foregoing examples have been described in some detail for purposes of clarity of understanding, the invention is not limited to the details provided. There are many alternative ways of implementing the invention.

What is claimed is:

1. A bone cage, comprising:
   a shaft extending from a head along a longitudinal axis to a tapered tip and including threads disposed on an external surface of the shaft;
   a cannula positioned within the shaft defined by a wall forming the shaft, the cannula extending from an opening in the head to another opening in the tip; and
   a plurality of fenestrations with fewer than three of the fenestrations having a same radial direction extending from any point along the longitudinal axis, at least some of the fenestrations extend through the threads on the shaft to the cannula, wherein the fenestrations omni-directionally located in the shaft such that the fenestrations cumulatively are open facing across substantially all radial directions of the cage.

2. The cage of claim 1, wherein the plurality of fenestrations define one or more helical rows.

3. The cage of claim 2, wherein the plurality of fenestrations define a plurality of helical rows.

4. The cage of claim 3, wherein the fenestrations that make up the helical rows have a longitudinal and angular position relative to adjacent fenestrations in a same helical row with the angular position corresponding to a circumferential gap, the adjacent fenestrations in the same helical row have a larger longitudinal distance between one another than the circumferential gap between one another.

5. The cage of claim 4, wherein a radial angular position between at least a pair of adjacent fenestrations in the helical row is less than 120°.

6. The cage of claim 4, wherein each of the plurality of helical rows define a different helix that has leads greater than the length of the cage.

7. The cage of claim 6, wherein each helix has fenestrations located at different axial locations than an adjacent helix.

8. The cage of claim 4, wherein multiple helixes of fenestrations extend along 90% or more of a length of the cage.

9. The cage of claim 2, wherein a radial angular position between the fenestrations on opposite ends of the helical row is less than 120°.

10. The cage of claim 2, wherein the shaft is uninterrupted extending distally from the last fenestration in a helical row to a tip of the shaft.

11. The cage of claim 1, wherein the tapered tip is a cutting tip configured to tap a predrilled hole.

12. The cage of claim 11, wherein the tapered tip includes a fluted edge that passes only though the threads and without passing below a minor diameter of the threads.

13. The cage of claim 1, wherein the shaft has a length to diameter ratio of between 5 and 1.5.

14. The bone cage of claim 1, wherein the shaft includes 5 or more angular segments with at least half of the angular segments having approximately a same cross-sectional access to the cannula such that each angular segment is able to deliver a generally consistent distribution of a therapeutic material through the fenestrations to the bone.

15. The bone cage of claim 14, wherein at least half of the angular segments have approximately a same number of fenestrations and a circumferential separation between adjacent fenestrations in the row is less than a diameter of the adjacent fenestrations.

16. A bone cage, comprising:
a shaft extending from a head to a tip along a longitudinal axis and including threads disposed on an external surface of the shaft;
a plurality of fenestrations defining a row disposed in a first helix;
wherein the first helix is defined by a helix angle measured from a line perpendicular to the longitudinal axis, to a direction of the first helix defined by respective positions of the plurality of fenestrations along at least a portion of the shaft, and
wherein at least four of the fenestrations of the plurality of fenestrations in the first helix extend directly through an otherwise uninterrupted portion of the thread; and
a cannula positioned within the shaft and extending from an opening in the head to another opening in the tip, wherein each of the fenestrations are defined by a wall that extends from an exterior of the shaft to the cannula.

17. The cage of claim 16, wherein adjacent fenestrations are separated by a gap greater than a pitch of the threads.

18. The cage of claim 16, wherein each fenestration in the helix row is separated from an adjacent fenestration in the row by a space greater than a diameter of the fenestration.

19. The cage of claim 16, wherein a first helix lead is greater than a length of the cage.

20. The cage of claim 16, wherein the shaft includes multiple rows of fenestrations with each row defining a different helix.

21. The cage of claim 16, wherein multiple helixes of fenestrations extend along 90% or more of a length of the cage.

22. The cage of claim 16, further comprising a tapered tip that is a cutting tip configured to tap a predrilled hole.

23. The cage of claim 16, wherein at least a portion of the shaft includes the plurality of fenestrations in an omni-directional orientation such that the fenestrations cumulatively are open facing across substantially all radial directions of the cage.

24. The cage of claim 16, wherein the cannula is configured to hold a material and the fenestrations are configured to allow the material in the cannula to flow there through to enter a joint at an exterior of the bone cage.

25. The bone cage of claim 16, further comprising a second plurality of fenestrations disposed in a second helix:
wherein the second helix is defined by a second helix angle measured from a line perpendicular to the longitudinal axis, to a direction of the second helix defined by respective positions of the second plurality of fenestrations along at least a portion of the shaft.

26. The bone cage of claim 16, wherein five or more of the fenestrations in the first helix extend directly through an otherwise uninterrupted portion of the thread.

27. The bone cage of claim 16, wherein the plurality of fenestrations avoid any features on an exterior of the shaft other than the thread.

28. A bone cage, comprising:
a shaft extending from a head to a tapered tip and including threads disposed on an external surface of the shaft;
a cannula positioned within the shaft defined by a wall forming the shaft, the cannula extending from an opening in the head to another opening in the tip; and
a plurality of fenestrations with at least some of the fenestrations extending through the threads on the shaft to the cannula;
wherein the shaft includes a longitudinal segment with the fenestrations being generally omni-directionally oriented such that;
the fenestrations cumulatively are open facing across substantially all radial directions of the cage, and
the segment is able to deliver therapeutic material through the fenestrations to a bone in generally evenly distributed intervals.

29. The cage of claim 28, wherein the plurality of fenestrations provide openings through 75-100% of radial outer surface directions of the shaft with the openings distributed along a longitudinal length of the segment.

30. The cage of claim 29, wherein longitudinal continuous strips of the shaft are present along the longitudinal segment, with the strips having radial angles of less than 10°.

31. The cage of claim 28, wherein the fenestrations are located in the shaft such that the shaft is omni-directional.

32. The cage of claim 28, wherein the plurality of fenestrations define one or more helical rows.

33. The cage of claim 32, wherein the plurality of fenestrations define a plurality of helical rows.

34. The cage of claim 33, wherein the fenestrations that make up the helical rows have a longitudinal and angular position relative to adjacent fenestrations in a same helical row, with the angular position corresponding to a circumferential gap, and the adjacent fenestrations in the same helical row have a larger longitudinal distance between one another than the circumferential gap between one another.

* * * * *